United States Patent
Tang et al.

(10) Patent No.: US 12,121,254 B2
(45) Date of Patent: Oct. 22, 2024

(54) SLIDE SLOT TYPE MULTI-ARM CLAMP

(71) Applicant: Micro-Tech (Nanjing) Co., Ltd., Jiangsu (CN)

(72) Inventors: Zhi Tang, Nanjing (CN); Mingqiao Fan, Nanjing (CN); Hongyan Jin, Nanjing (CN); Ning Li, Nanjing (CN); Changqing Li, Nanjing (CN); Jiefeng Xi, Nanjing (CN); Jianyu Wei, Nanjing (CN)

(73) Assignee: Micro-Tech (Nanjing) Co., Ltd., Nanjing (CN)

( * ) Notice: Subject to any disclaimer, the term of this patent is extended or adjusted under 35 U.S.C. 154(b) by 465 days.

(21) Appl. No.: 17/517,921

(22) Filed: Nov. 3, 2021

(65) Prior Publication Data

US 2022/0054156 A1    Feb. 24, 2022

Related U.S. Application Data

(63) Continuation of application No. PCT/CN2019/125021, filed on Dec. 13, 2019.

(30) Foreign Application Priority Data

May 5, 2019    (CN) .................. 201910368716.X

(51) Int. Cl.
    *A61B 17/29*    (2006.01)
(52) U.S. Cl.
    CPC ...... *A61B 17/29* (2013.01); *A61B 2017/2902* (2013.01); *A61B 2017/2906* (2013.01);
(Continued)

(58) Field of Classification Search
    CPC ..... A61B 17/29; A61B 17/10; A61B 17/1285; A61B 2017/2902; A61B 2017/2931; A61B 2017/2938
    See application file for complete search history.

(56) References Cited

U.S. PATENT DOCUMENTS

| | | |
|---|---|---|
| 2005/0107809 A1 | 5/2005 | Litscher et al. |
| 2007/0167978 A1 | 7/2007 | Yamamoto et al. |

(Continued)

FOREIGN PATENT DOCUMENTS

| | | | |
|---|---|---|---|
| CN | 103989500 A | | 8/2014 |
| CN | 203828993 | * | 9/2014 |

(Continued)

OTHER PUBLICATIONS

International Search Report issued on Mar. 2, 2020 in corresponding application No. PCT/CN2019/125021, 6 pgs.
(Continued)

*Primary Examiner* — Brooke Labranche
(74) *Attorney, Agent, or Firm* — Maier & Maier, PLLC

(57) ABSTRACT

A slide slot type multi-arm clamp includes a handle, a catheter, a clamping portion, a spring tube and a control line. In practical applications, a surgical operator applies an axial thrust and a pulling force to the handle to drive the control line to move, so as to open/close and lock the clamping portion. Moreover, side clamp arms and a clamp base in the clamping portion can be easily separated from the catheter or the spring tube to stay in a human body so as to achieve the functions of hemostasis and tissue suture. The side slot type multi-arm clamp can achieve the effect of minimizing the length of the instrument retained in the human body by the cooperation between the side clamp arms and the clamp base.

9 Claims, 7 Drawing Sheets

(52) U.S. Cl.
CPC .............. *A61B 2017/2911* (2013.01); *A61B 2017/2934* (2013.01)

(56) References Cited

U.S. PATENT DOCUMENTS

| | | |
|---|---|---|
| 2015/0351771 A1 | 12/2015 | Malkowski et al. |
| 2016/0317179 A1 | 11/2016 | Kawashima et al. |
| 2020/0205836 A1 * | 7/2020 | Uesaka .............. A61B 17/1285 |

FOREIGN PATENT DOCUMENTS

| | | | |
|---|---|---|---|
| CN | 203828993 | U | 9/2014 |
| CN | 104586444 | A | 5/2015 |
| CN | 104605910 | A | 5/2015 |
| CN | 106236182 | A | 12/2016 |
| CN | 206239447 | * | 6/2017 |
| CN | 206239447 | U | 6/2017 |
| CN | 108523945 | A | 9/2018 |
| CN | 109009254 | A | 12/2018 |
| CN | 109044474 | A | 12/2018 |
| CN | 109303589 | A | 2/2019 |
| CN | 109805986 | A | 5/2019 |
| CN | 109953800 | A | 7/2019 |
| EP | 3281588 | A1 | 2/2018 |
| WO | 2013166866 | A1 | 11/2013 |

OTHER PUBLICATIONS

Notification of Grant of Patent Rights for Invention Application issued on Sep. 7, 2023, in corresponding Chinese Application No. 201910368716.X, 12 pages.

* cited by examiner

SLIDE SLOT TYPE MULTI-ARM CLAMP

CROSS-REFERENCE TO RELATED APPLICATIONS

This application is a continuation of International Application No. PCT/CN2019/125021, filed on Dec. 13, 2019, which claims priority to Chinese Patent Application No. 201910368716.X, field on May 5, 2019. Both of the applications are hereby incorporated by reference in their entireties.

TECHNICAL FIELD

The present application relates to the field of medical instruments, and in particular, to a slide slot type multi-arm clamp.

BACKGROUND

Endoscopic EMR (endoscopic mucosal resection) and ESD (endoscopic sub-mucosal dissection) have a high cure rate for early cancer and are widely used in clinical practice. For the endoscopic mucosal resection and sub-mucosal dissection, postoperative wound suture is required using forceps or clamps suitable for endoscopic environment.

In practical applications, the operating space under the endoscope is small, and the working cavity channel through the endoscope is small. For a bleeding part with a large wound in the physiological bending of the human body, the existing forcep or clamp products have a limited opening width, usually 11 mm, after they reach the lesion site, and for an oversized 50 mm wound, they cannot cover the entire wound. Therefore, in order to treat the oversized wound, the endoscopic doctor requires to perform the purse type suture, in which first a ring-shaped plastic ring is set, then an existing small-opening clamp arms or clamps are placed in a denser piling way along the plastic ring around the wound, finally the tail of the plastic ring is hooked by using a special releaser hook for the plastic ring, so as to tighten the plastic ring. Due to that the line on the plastic ring and the wound tissue are clamped simultaneously by the clamp arm or the clamp, all clamp arms and clamps are closed together when the ring is tightened, and the oversized 50 mm wound can be sutured.

However, the above method is complicated in operating, which causes a long operation time. Moreover, when the plastic ring is tightened, the clamp arms or heads of the clamps will flip and sink into the wound, which is not conductive to nature shedding after surgery; therefore the endoscopic doctor will need to be more careful to tighten the ring; if flipping occurs, the ring is opened again and the clamp arms or clamp head are turned over by other instrument and then tightened, thereby the operation time is extended again and the success rate is further reduced.

SUMMARY

The present application provides a slide slot type multi-arm clamp to solve the problem of complicated operation and low success rate of traditional suture clamp of large wound.

The present application provides a slide slot type multi-arm clamp for the hemostasis and tissue suture of the digestive tract under the guidance of an endoscope, including: a handle, a catheter, a lamping portion, and a control line, where a proximal end of the catheter is connected with the handle; the clamping portion is connected detachably with a distal end of the catheter; the control line is provided inside the catheter so as to connect the clamping portion and the handle.

The clamping portion includes at least two side clamp arms, at least one middle clamp arm and a clamp base; the side clamp arms are provided a moving slide slot, the clamp base is provided with a pin axis, the pin axis can slide in the moving slide slot to control opening and closing of the side clamp arms; a protruding part is provided at the distal end of the moving slide slot, so as to restrict the pin axis to the distal end of the moving slide slot and lock the side clamp arms; and the middle clamp arm is connected fixedly to the clamp base; and the number of the control line is the same as the number of the side clamp arms, each control line is connected separately with the side clamp arms to independently control the opening and closing of the side clamp arms.

Optionally, the protruding part includes a buffer cavity and a limiting protrusion; the limiting protrusion protrudes on a side wall of the moving slide slot; the buffer cavity is a through hole provided on the side clamp arms, and near the distal end of the moving slide slot, so that the limiting protrusion forms a beam structure.

Optionally, the slide slot type multi-arm clamp further includes a spring tube connected with the catheter, the spring tube is a cylindrical tube sheath surrounding the control line; the spring tube is connected detachably with the clamp base.

Optionally, the proximal end of the clamp base is a round tubular structure, multiple arc-shaped protrusions are provided evenly on a side wall of the round tubular structure; the spring tube is provided round holes, which is cooperated with the arc-shaped protrusions, to achieve a detachable connection with the clamp base.

Optionally, the clamping portion further includes a separation claw connected with the clamp base; the separation claw includes a pulling part connected with the control line, and multiple deformable connecting arms provided on the pulling part.

The spring tube or the clamp base is provided with a plurality of holes for fixing the connecting arms, and when a pulling force of the control line increases to a deformation limit of the connecting arms, the connecting arms are separated from the spring tube or the clamp base.

Optionally, a connecting tube is provided on the control line, the control line runs through the connecting tube; the connecting tube is contacted with the pulling part to pull the separation claw.

Optionally, a step is provided in a middle of the clamp base; a tail hook is provided at a proximal end of the side clamp arms, the side clamp arms are locked by cooperation between the tail hook and the step.

Optionally, a connecting post is provided at a distal end of the control line, a tail hole is provided at a proximal end of the side clamp arms, the tail hole is a semi-opening round hole or long round hole to accommodate the connecting post, and when a pulling force of the control line is greater than the deformation limit of the tail hole, the connecting post slides out of the tail hole.

Optionally, the side clamp arm and the middle clamp arm are further provided with a clamping tooth, to enhance a clamping ability of the side clamp arms and the middle clamp arm on a tissue.

Optionally, the handle includes a handle body, and at least two slidable members that are independent of each other and slidably connected to the handle body; the handle body is a hollow structure, each slidable member is connected with one side clamp arm through one control line in the handle body.

Optionally, a rotating portion in a polygonal structure is provided at the proximal end of the catheter, the rotating portion is provided with a rotating member with a polygonal inner bore to make the rotating member be slidably connected with the rotating portion; and an anti-skid rubber ring is provided on an inner wall of the rotating member.

According to the above technical solutions, the present application provides a slide slot type multi-arm clamp, including a handle, a catheter, a clamping portion, a spring tube and a control line. In practical applications, a surgical operator applies an axial thrust and a pull force to the handle, to drive the control line to move, so as to open/close and lock the clamping portion. Moreover, the side clamp arm and the clamp base in the clamping portion can be easily separated from the catheter or the spring tube, so as to stay in a human body to achieve the functions of hemostasis and tissue suture. The side slot type multi-arm clamp provided in the present application can achieve the effect of minimizing the length of the instrument retained in the human body by the cooperation between the side clamp arm and the clamp base. Moreover, the structure of the moving slide slot on the side clamp arm can achieve accurate and repeatable opening and closing, simplify the operation, and improve the success rate.

DETAILED DESCRIPTION OF EMBODIMENTS

The embodiments will be described below in detail with examples shown in the accompanying drawings. Unless otherwise indicated, the same numerals in different figures indicate the same or similar elements when the following description refers to the drawings. The implementations described in the following embodiments do not represent all implementations consistent with the present application. These are just examples of systems and methods consistent with some aspects of the present application as detailed in the claims.

It should be noted that, in the technical solutions provided in the present application, for ease of description, an end of the apparatus disposed inside the human body is called a distal end, and this end is mainly used to perform an surgical action on a tissue; an end located outside the body is called a proximal end, and this end is mainly used for a surgical operator to operate. Unless otherwise specified in the present application, the distal end of each part refers to an end close to inside of the body, the proximal end of each part refers to an end close to outside of the body.

Figure 1:
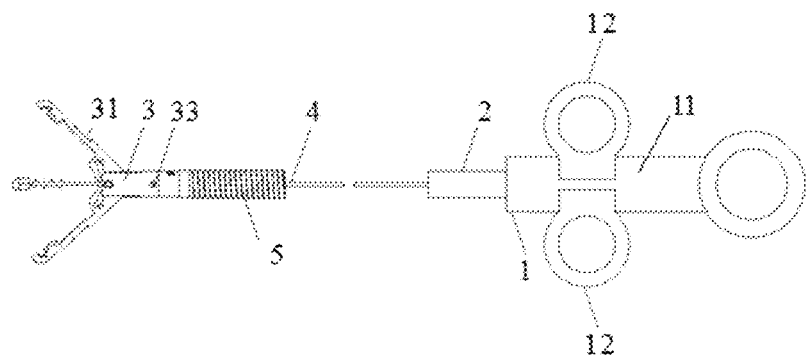
FIG. 1 is a schematic structural diagram of a slide slot type multi-arm clamp of the present application.
Figure 2:
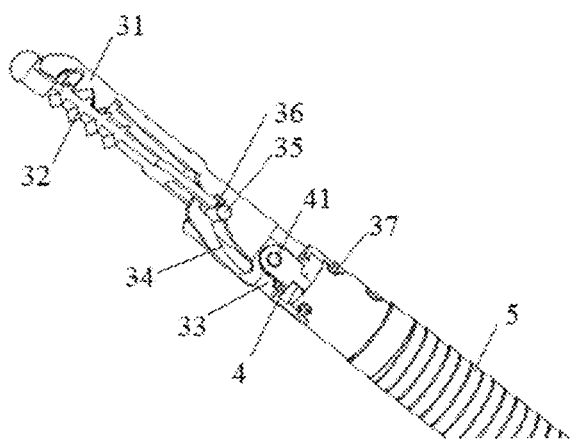
FIG. 2 is a schematic diagram of a three-dimensional structure of a slide slot type multi-arm clamp of the present application.

Referring to FIG. 1, which is a schematic structural diagram of a slide slot type multi-arm clamp of the present application. According to FIG. 1 and FIG. 2, the slide slot type multi-arm clamp provided in the present application, includes: a handle 1, a catheter 2, a clamping portion 3, a control line 4 and a spring tube 5. Among them, the handle 1 is used to perform a surgical operation, and is a direct operation and control part of a surgical operator.

In the technical solution of the present application, due to the operator is required to apply an axial thrust and a pulling force to the handle 1 to drive the control line 4 to move, so as to open/close and lock the clamping portion 3, the handle 1 may further include a handle body 11, and at least two slidable members 12 that are independent with each other and slidably connected to the handle body 11. The handle body 11 is a hollow structure, and each slidable member 12 in the handle body 11 is connected with one side clamp arm 31 by one control line 4.

Among them, the slidable members 12 may be two rings disposed on the handle body 11, and in practical applications, the two rings as the slidable members 12 can be separately sleeved on two fingers, such as index finger and middle finger. A tail end of the handle body 11 is also provided with a ring, and the ring on the tail end is used to be sleeved on the thumb, so as to move the slidable members 12 via a finger pinching force.

The proximal end of the catheter 2 is connected with the handle 1, and in order to adapt the structure of the alimentary canal and the channel shape of endoscopic forceps, the catheter 2 can be a soft round tube, such as plastic hose. Furthermore, the interior thereof is provided with a supporting spring extending in a helical manner, so that when the catheter 2 is pressed by the side wall tissue of the alimentary canal, the catheter 2 is still capable of maintaining a tubular state and avoiding actions that affect the interior device. The length of the catheter 2 in the present application should satisfy a distance capable of performing a surgical operation outside the body.

Figure 3:
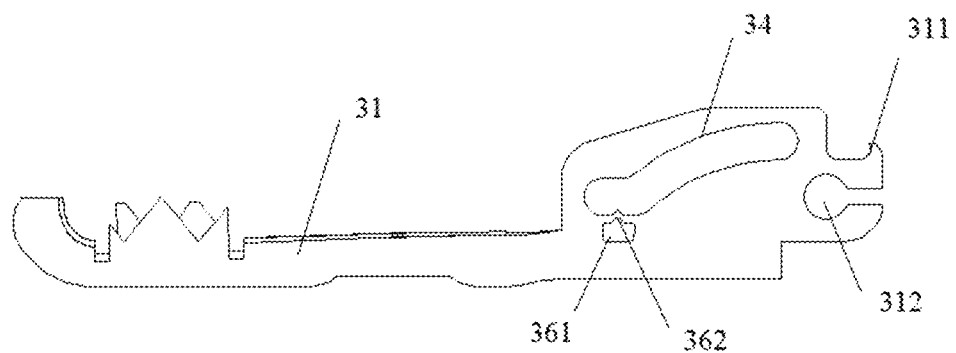
FIG. 3 is a schematic structural diagram of a side clamp arm of the present application.
Figure 4:
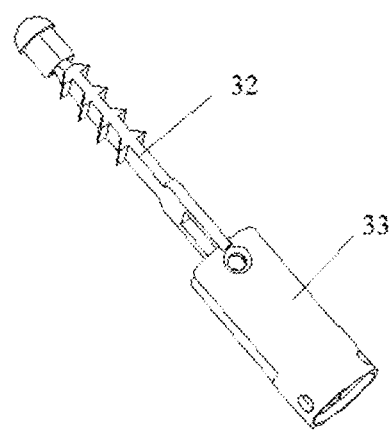
FIG. 4 is a schematic structural diagram of a clamp base of the present application.

The clamping portion 3 can be connected detachably with the distal end of the catheter 2. The clamping portion 3 is opened and closed by the action control of the operator. Therefore, in the technical solution provided in the present application, as shown in FIG. 3, the clamping portion 3 includes at least two side clamp arms 31, at least one middle clamp arm 32 and a clamp base 33; the side clamp arms 31 are provided a moving slide slot 34, the clamp base 33 is provided a pin axis 35, and the pin axis 35 can slide inside the moving slide slot 34 to control the opening/closing of the side clamp arms 31; the distal end of the moving slide slot 34 is provided with a protruding part 36, so as to restrict the pin axis 35 to the distal end of the moving slide slot 34 and lock the side clamp arms 31; as shown in FIG. 4, the middle clamp arm 32 is fixedly connected with the clamp base 33.

The moving slide slot 34 can be L-shaped, blunt angle-shaped, arc-shaped and other forms in order to achieve the closure of the clamp arms. In practical applications, taking a three-arm clamp as an example, the three-arm clamp can includes two side clamp arms 31 and one middle clamp arm 32, and under the action of the pin axis and the moving slide slot 34, the side clamp arms 31 may produce a clamping action relative to the middle clamp arm 32, so as to clamp the tissue. Further, as shown in the FIG. 3, FIG. 4 and FIG. 8, the side clamp arms 31 and the middle clamp arm 32 are provided a clamping tooth to enhance the clamping ability of the side clamp arms 31 and the middle clamp arm 32 on the tissue.

The control lines 4 are provided inside the catheter 2 so as to be connected with the clamping portion 3 and the handle 1. Moreover, the number of the control lines 4 is the same as the number of the side clamp arms 31, and each control line 4 is connected with the side clamp arms 31 to independent control the opening/closing of the side clamp arms 31.

In the practical application of the slide slot type multi-arm clamp provided in the present application, due to the existence of multiple clamp arms, they can be respectively relatively opened and closed for a large wound, so as to pull tissue of the large wound, that is, one side clamp arm 31 and the middle clamp arm 32 respectively open and clamp one side of the tissue, and move to other side of the tissue and open again under the drive of the endoscope, so that another side clamp arm 31 and the middle clamp arm 32 close and clamp the tissue, so as to perform successful suture even though the opening size of the wound is much larger than the maximum opening size of the clamp.

Figure 8:
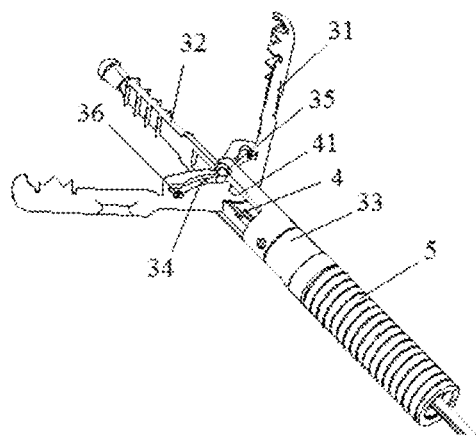
FIG. 8 is a schematic structural diagram of an opening state of a clamping portion of the present application.

In the technical solution of the present application, as shown in FIG. 8, when the operator intends to close one side clamp arm 31, he can pull the slidable member 12 corresponding to the handle 1 so that the slidable member 12 drives the control line 4 to pull the side clamp arm 31 to move back, thereby enabling the pin axis 35 to move from the proximal end of the moving slide slot 34 to the distal end thereof. At this time, due to the action between the edge of the L-shaped or other shaped moving slide slot 34 and the pin axis 35, the side clamp arm 31 moves closer to the middle clamp arm 32 to clamp the tissue.

If the operator continues to pull the slidable member 12, the pin axis 35 will further move toward the distal end of the moving slide slot 34, and the pin axis 35 will contact the protruding part 36. Since the protruding part 36 has deformation ability, when the protruding part 36 is pressed by the pin axis 35, it deforms so that the pin axis 35 passes over the protruding part 36 and reaches the farthest distal end of the moving slide slot 34. At this time, the side clamp arm 31 and the middle clamp arm 32 always remain a closed state, and are restricted by the protruding part 36, and the pin axis 35 is not easy to move in the opposite direction at the distal end of the moving slide slot 34, which achieves the locking effect.

Further, as shown in FIG. 3, the protruding part 36 includes a buffer cavity 361 and a limiting protrusion 362; the limiting protrusion 362 protrudes on a side wall of the moving slide slot 34; the buffer cavity 361 is a through hole provided on the side clamp arm 31 and close to the distal end of the moving slide slot 34, so that the limiting protrusion 362 forms a beam structure. In the present embodiment, the protruding part 36 is presented as a beam structure as a whole, and such beam structure can provide a retracting space for the limiting protrusion 362 via the structure of the buffer cavity 361, to facilitate deformation.

Moreover, in the practical application, such beam structure can provide support on both ends of the limiting protrusion 362, and thus the connection stability of the whole protruding part 36 is high. Specifically, in the practical application if corresponding protruding part 36 uses a material that is prone to deformation, it will limit the overall locking capacity to a certain extent, and as the clamping time increases, the protruding part 36 is prone to produce inelastic deformation, i.e., changing the design structure of the protruding part 36, it is very difficult to maintain the locking effect of the original design.

However, if a material that is not prone to deformation is used, the pulling force required during the operation process is relatively large, which brings inconvenience for the operator. Therefore, this embodiment can acquire deformation more easily under the same material by the protruding part 36 in beam structure; moreover, due to the support of the both sides of the beam structure, the possibility of non-elastic deformation can also be reduced and the stability of the protruding part 36 can be improved.

In order to achieve a detachable connection between the catheter 2 and the clamping portion 3, in some embodiments of the present application, the slide slot type multi-arm clamp further includes a spring tube 5 connected with the catheter 2, the spring tube 5 is a cylindrical tube sheath surrounding the control line 4; the spring tube 5 is connected detachably with the clamp base 33. In a practical application, in order to simplify the structure, the spring tube 5 and the catheter 2 can be made into the same structure.

Specifically, in one embodiment, the proximal end of the clamp base 33 is a round tubular structure, a plurality of arc-shaped protrusions are provided evenly on a side wall of the round tubular structure; the spring tube 5 is provided with a round hole cooperated with the arc-shaped protrusions so as to be connected detachably with the clamp base 33. In the present embodiment, by setting the plurality of protrusions on the round tubular portion of the clamp base 33, during the closing process of the clamp arm, the plurality of protrusions are kept in the round hole of the spring tube 5 so as to be pulled by the control line 4 to move. After the pin axis 4 reaches the farthest distal end of the moving slide slot 34, the pulling force on the slidable member 12 is increased, so that the protrusions on the clamp base 33 slide out of the round hole to achieve separation.

Figure 7:
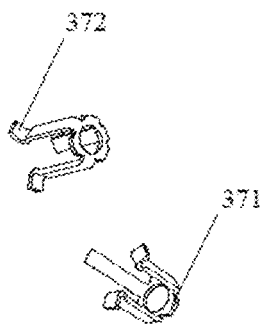
FIG. 7 is a schematic structural diagram of a separation claw of the present application.

In another embodiment of the present application, as shown in FIG. 7, the clamping portion 3 further includes a separation claw 37 connected with the clamp base 33; the separation claw 37 includes a pulling part 371 connected with the control line 4, and multiple deformable connecting arms 372 provided on the pulling part 371. The spring tube 5 and/or the clamp base 33 are provided with multiple holes for fixing the connecting arms 372, and when the pulling force of the control line 4 is increased to the deformation limit of the connecting arms 372, the connecting arms 372 are separated from the spring tube 5 and/or the clamp base 33.

Figure 5:
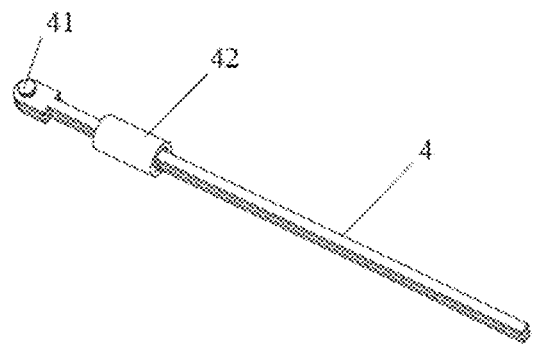
FIG. 5 is a schematic structural diagram of a control line of the present application.

Further, as shown in FIG. 5, the control line 4 is provided with a connecting tube 42, the control line 4 runs through the connecting tube 42; the connecting tube 42 is contacted with the pulling part 371 to pull the separation claw 37. In the present application, the separation claw 37 has multiple connecting arms 372 in the circumferential direction, the connecting arms 372 can be combined with the holes on the clamp base 33 and/or the spring tube 5, all portions of the pulling part 371 are connected to the control line 4 at the same time, and under the pulling force of the control line 4, the connecting arms 372 are deformed and thus separated from the clamp base 33 and/or the spring tube 5, so as to achieve the effective separation of the clamp base from the spring tube.

Figure 9:
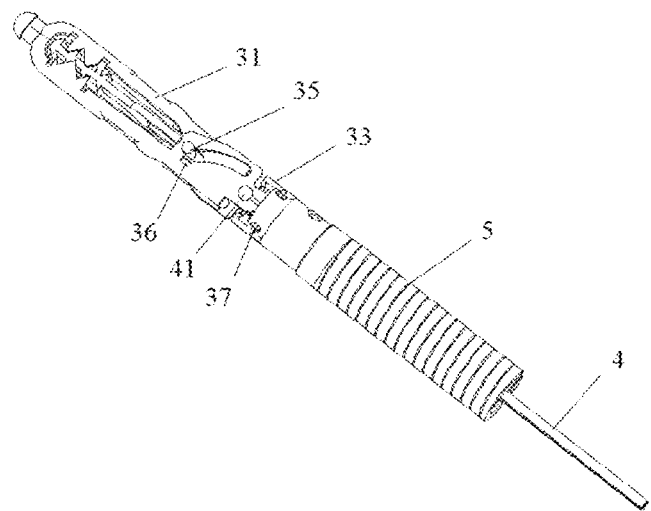
FIG. 9 is a schematic structural diagram in a state in which a clamping portion is closed and a connecting post is not separated according to the present application.

In some embodiments of the present application, as shown in FIG. 3 and FIG. 9, the distal end of the control line 4 is provided with a connecting post 41, the proximal end of the side clamp arm 31 is provided with a tail hole 312, the tail hole 312 is a semi-opening round hole or long round hole and is used to accommodate the connecting post 41, and when the pulling force of the control line 4 is greater than the deformation limit of the tail hole 312, the connecting post 41 slide out of the tail hole 312. In practical application, the tail hole 41 is connected with the connecting post 312 of the control line 4 so as to drive the clamping portion 3 as a whole to reciprocate by the connecting post 41.

Correspondingly, as shown in FIG. 5, in order for the control line 4 to transmit torque better and for the connecting post 41 to have compliant performance so as to smoothly pass through the endoscopic channel, the control line 4 can be made of a single filament, a single sheet or multi-strand wires. The distal end of the control line 4 is provided with the fixed connecting post 41. Moreover, the control line 4 is further provided with the connecting tube 42, the connecting tube 42 can separate the control line 4, and a section of the control line 4 at the proximal end can be made of a single filament, a single sheet or multi-strand wires, and has a high hardness to transmit axial force and rotational torque.

Figure 6:
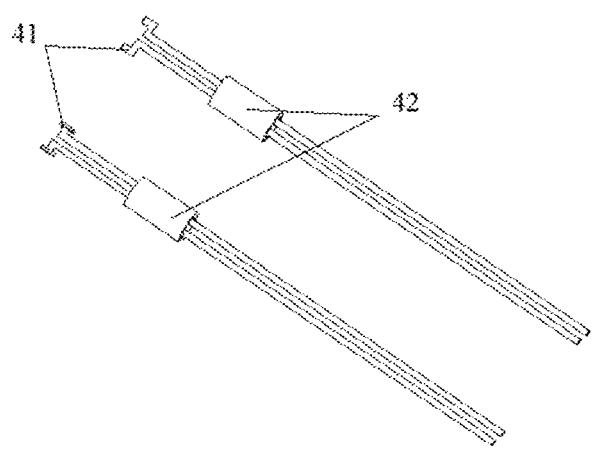
FIG. 6 is a schematic structural diagram of another control line of the present application.

The connecting tube 42 can be separated from a section of the control line 4 close to the proximal end, or can be made into a whole. In the present embodiment, the connecting post 41 can be a cylindrical structure disposed on the side of the control line 4, and for convenient transmission of the force torque, the connecting post 41 is not limited to the cylindrical structure, but can also be a T-shaped or Z-shaped structure, as shown in FIG. 6, to enhance the stability of the connection between the control line 4 and the side clamp arms 31.

As shown in FIG. 3, FIG. 4 and FIG. 9, a step is provided at the middle portion of the clamp base 33; the proximal end of the side clamp arms 31 are provided a tail hook 311, the side clamp arms 31 are locked by the cooperation between the tail hook 311 and the step. In practical application, when two side clamp arms 31 are in a closed but unlocked state, the protruding part 36 can restrict the pin axis 35 from advancing, so as to achieve the closed but unlocked state of the clamp arms.

The contact between the tail hook 311 provided at the proximal end of the side clamp arms 31 and the restricting step of the middle of the clamp base 33 increases the movement resistance of the pin shaft 35 and achieves the closed but unlocked state of the clamp arms. At this time, if the medical worker confirms that the clamping operation is wrong, and they need to reopen the clamp arms, it is possible to drive the slidable member 12 on the handle 1 to move forward, and thus the control line 4 is driven to drive the side clamp arms 31 to move forward, and by using the cam principle, under the condition of stationary relative to the pin axis 35, the side clamp arm 31 is enabled to be reopened along the shape of the moving slide slot 34.

Figure 10:
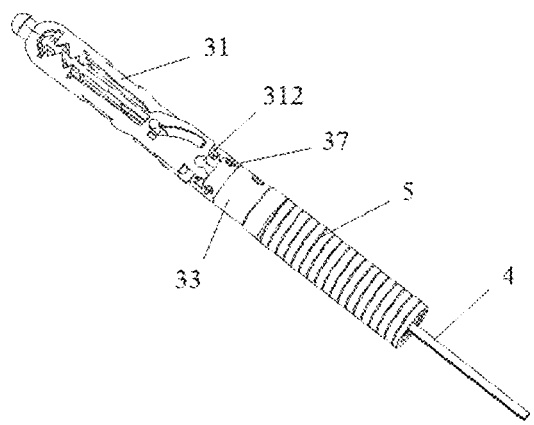
FIG. 10 is a schematic structural diagram in a state in which a clamping portion is closed and a connecting post is separated according to the present application.

As shown in FIG. 9, when the medical worker confirms the tissue is clamped correctly, by pulling the slidable member 12 on the handle 1 backward, the control line 4 is driven to move backward and thus drive the side clamp arms 31 to continue to move backward. When the applied force is greater than the force of the protruding part 36 restricting the pin axis 35, the pin axis 35 passes over the protruding part 36 and enters the farthest distal end of the moving slide slot 34. At this time, as shown in FIG. 10, the tail hook 311 at the proximal end of the side clamp arm 31 produces deformation and enters the step of the middle of the clamp base 33. With further increase of the force of the control line 4, the tail hook 311 rotates or deforms laterally and is hooked on the step in the middle of the clamp base 33 to achieve locking in the axial direction, and at this time, the side clamp arm 31 cannot be re-opened.

Figure 11:
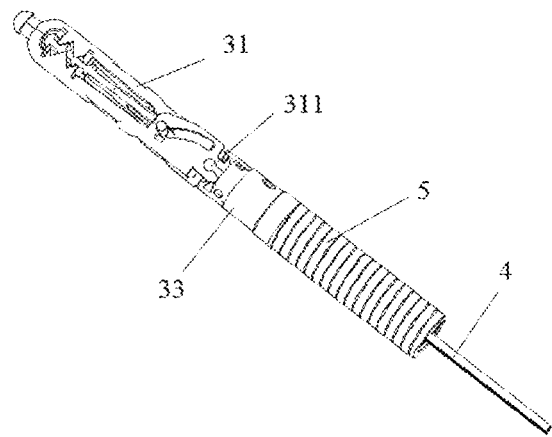
FIG. 11 is a schematic structural diagram in a state in which a clamping portion is closed and a separation claw is separated according to the present application.
Figure 12:
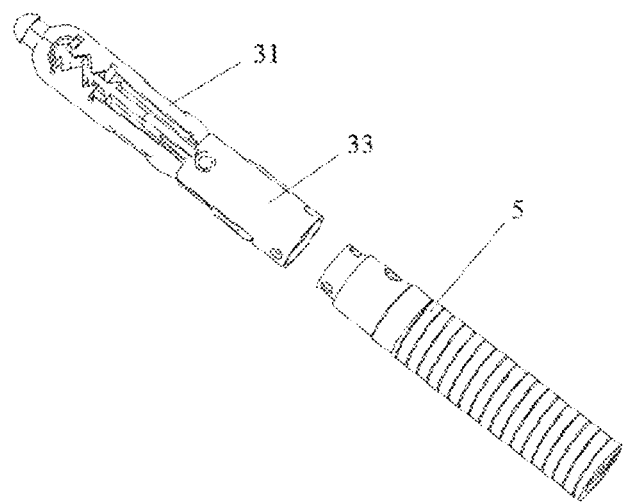
FIG. 12 is a schematic structural diagram of a clamping portion in a completely separated state according to the present application.

Finally, as shown in FIG. 11, when two side clamp arms 31 are in a closed state, the control line 4 moves backward, and the separation claw 37 is pull out by the connecting tube 42 on the control line 4. With the operation of the medical worker, the control line 4 continues to move backward, and the control line 4 is pulled into the spring tube 5 so as to completely separate the spring tube 5 from the clamp base 33, and the operation is over, as shown in FIG. 12.

Figure 13:
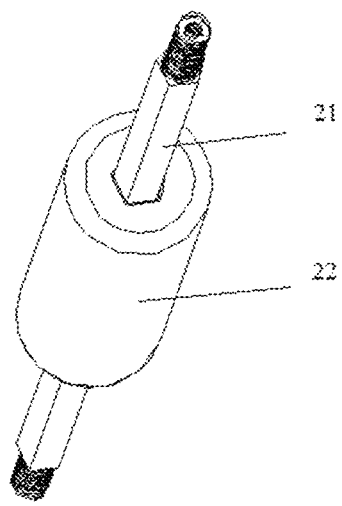
FIG. 13 is a schematic structural diagram of a rotating portion of the present application.

Further, as shown in FIG. 13, the proximal end of the catheter 2 is provided with a rotating portion 21 in a polygonal structure, the rotating portion 21 is provided with a rotating member 22 with a polygonal inner bore, so that the rotating member 22 is slidably connected with the rotating portion 21; the inner wall of the rotating member 22 is further provided with an anti-skid rubber ring. In clinical use, the catheter 2 or the spring tube 5 have a small diameter, generally less than 2.8 mm, and thus the hand feeling is very poor during operation, and it is not easy to hold for rotation operation. Thus, in the present embodiment, a part of the catheter 2 that has not entered the endoscope is an outer pentagon. In order to reduce the rotational friction resistance, a part of the catheter 2 or the spring tube 5, which has entered the endoscope, is circular, so that the torque can be transmitted outside the endoscope through rotating the pentagon.

In order to acquire a better operating experience, in the present embodiment, another rotating member 22 is added to the pentagonal rotating portion 21, the inner bore of this rotating member 22 is also pentagonal, and thus the rotating member 22 fits with the rotating portion 21 in shape to drive the rotating portion 21 to rotate but the rotating member 22 itself does not rotate relative to the rotating portion 21, but the rotating member 22 can slide at any position of the catheter 2, so that the doctor can adjust the rotation position suitable for himself as needed. In order to prevent this rotating member 22 from sliding too loosely on the catheter 2, a rubber ring can be added to the inner bore of the rotating member 22 so as to increase a certain resistance, for example, less than 2N. In this way, the rotating member 22 not only can slide on the catheter 2 to adjust a suitable position, but also can rotate at any position.

According to the above technical solutions, the present application provides a slide slot type multi-arm clamp, including: a handle 1, a catheter 2, a clamping portion 3, a spring tube 5 and a control line 4. In actual application, the surgical operator applies an axial thrust and a pull force to the handle 1 to drive the control line 4 to move, so as to open/close and lock the clamping portion 3. Moreover, the side clamp arms 31 and the clamp base 33 in the clamping portion 3 can be easily separated from the catheter 2 or the spring tube 5 to stay in a human body, achieving the functions of hemostasis and tissue suture. The slide slot type multi-arm clamp provided in the present application can minimize the length of the instrument retained in the human body by the cooperation between the side clamp arms 31 and the clamp base 33. Moreover, the structure of the moving slide slot 34 on the side clamp arms 31 can achieve accurate and repeatable opening and closing, simplify the operation, and improve the success rate.

The similar parts between the embodiments provided in the present application can be referred to each other, the specific implementations provided above are merely some exemplary examples in the general concept of the present application, and do not constitute a limitation of the protection scope of the present application. For those of ordinary skill in the art, all other implementations expanded based on the solutions of the present application without creative efforts shall fall within the protection scope of the present application.

What is claimed is:

1. A slide slot type multi-arm clamp, comprising:
   a handle;
   a catheter, a proximal end of which is connected with the handle;
   a clamping portion, which is connected detachably to a distal end of the catheter;
   control lines, which are provided inside the catheter so as to connect the clamping portion and the handle;
   wherein the clamping portion comprises at least two side clamp arms, at least one middle clamp arm and a clamp base; the side clamp arms are provided with moving slide slots, respectively, and the clamp base is provided with a pin axis, and the pin axis is slidable within the moving slide slots to control opening and closing of the side clamp arms; protruding parts are provided at distal ends of the moving slide slots, respectively, so as to restrict the pin axis to the distal ends of the moving slide slots and lock the side clamp arms; the middle clamp arm is connected fixedly with the clamp base;
   the number of the control lines is the same as the number of the side clamp arms, each side clamp arm is connected to a respective control line for independently controlling the opening and closing of the side clamp arm,
   wherein each protruding part comprises a buffer cavity and a limiting protrusion; the limiting protrusion is protruded on a side wall of a respective moving slide slot; the buffer cavity is a through hole provided on a respective side clamp arm and near the distal end of the moving slide slot, so that the limiting protrusion forms a beam structure.

2. The slide slot type multi-arm clamp according to claim 1, wherein the slide slot type multi-arm clamp further comprises a spring tube connected with the catheter, the spring tube is a cylindrical tube sheath surrounding the control lines; the spring tube is connected detachably with the clamp base.

3. The slide slot type multi-arm clamp according to claim 2, wherein a proximal end of the clamp base is a round tubular structure, a plurality of arc-shaped protrusions are provided evenly on a side wall of the round tubular structure; the spring tube is provided with a round hole cooperated with the arc-shaped protrusions to achieve a detachable connection with the clamp base.

4. The slide slot type multi-arm clamp according to claim 2, wherein the clamping portion further comprises a separation claw connected with the clamp base; the separation claw comprises a pulling part connected with the control lines, and a plurality of deformable connecting arms provided on the pulling part;
   at least one of the spring tube and the clamp base are provided with a plurality of holes for fixing the connecting arms, and when a pulling force of the control line increases to a deformation limit of the connecting arms, the connecting arms are separated from at least one of the spring tube and the clamp base.

5. The slide slot type multi-arm clamp according to claim 4, wherein each control line is provided with a respective connecting tube, each control line runs through the connecting tube; the connecting tube is contacted with the pulling part to pull the separation claw.

6. The slide slot type multi-arm clamp according to claim 1, wherein a step is provided in a middle of the clamp base; a tail hook is provided at a proximal end of the side clamp arms, the side clamp arms are locked by cooperation between the tail hook and the step.

7. The slide slot type multi-arm clamp according to claim 1, wherein a respective connecting post is provided at each distal end of each control line, a tail hole is provided at a proximal end of the side clamp arms, the tail hole is a semi-opening round hole or long round hole to accommodate the connecting post, and when a pulling force of each control line is greater than a deformation limit of the tail hole, the connecting post slides out of the tail hole.

8. The slide slot type multi-arm clamp according to claim 1, wherein the side clamp arms and the middle clamp arm are further provided with a clamping tooth, so as to enhance a clamping ability of the side clamp arms and the middle clamp arm on a tissue.

9. The slide slot type multi-arm clamp according to claim 1, wherein a rotating portion in a polygonal structure is provided at the proximal end of the catheter, the rotating portion is provided with a rotating member with a polygonal inner bore, so as to make the rotating member be slidably connected with the rotating portion; and an anti-skid rubber ring is provided on an inner wall of the rotating member.

* * * * *